United States Patent
Kim et al.

(10) Patent No.: US 8,048,648 B2
(45) Date of Patent: Nov. 1, 2011

(54) CORYNEBACTERIUM GLUTAMICUM VARIETY PRODUCING L-ARGININE AND METHOD FOR FABRICATING THE SAME

(75) Inventors: Hye Won Kim, Seongnam-si (KR); Hyejin Choi, Seoul (KR); Ji-Hye Lee, Anyang-si (KR); Soo Youn Hwang, Yongin-si (KR)

(73) Assignee: CJ Cheil Jedang Corporation, Seoul (KR)

( * ) Notice: Subject to any disclaimer, the term of this patent is extended or adjusted under 35 U.S.C. 154(b) by 13 days.

(21) Appl. No.: 12/522,280

(22) PCT Filed: Jan. 11, 2008

(86) PCT No.: PCT/KR2008/000204
§ 371 (c)(1),
(2), (4) Date: Jul. 7, 2009

(87) PCT Pub. No.: WO2008/088148
PCT Pub. Date: Jul. 24, 2008

(65) Prior Publication Data
US 2010/0041109 A1    Feb. 18, 2010

(30) Foreign Application Priority Data
Jan. 18, 2007 (KR) .................. 10-2007-0005831

(51) Int. Cl.
*C12P 13/10* (2006.01)
*C12N 1/20* (2006.01)
(52) U.S. Cl. .................. 435/114; 435/252.3; 435/252.32

(58) Field of Classification Search .................. None
See application file for complete search history.

(56) References Cited

FOREIGN PATENT DOCUMENTS
WO    WO 01/00843    1/2001
WO    WO 01/66573    9/2001

OTHER PUBLICATIONS

McHardy et al. ( J. Biotechonol 2003, 104, pp. 229-240).*
Sousa et al. Microbiology 148(Pt5):1291-1303, 2002.*
European Search Report dated Dec. 11, 2009 re EP Appln. No. EP 08 70 4743.

* cited by examiner

*Primary Examiner* — Tekchand Saidha
*Assistant Examiner* — Younus Meah
(74) *Attorney, Agent, or Firm* — Brinks Hofer Gilson & Lione

(57) ABSTRACT

The present invention relates to an L-arginine producing mutant strain, and a method for fabricating the same. In particular, the present invention relates to a polynucleotide comprising an argD2 gene (Ncgl2355) that is a putative gene of acetylornithine aminotransferase involved in arginine biosynthesis of *Corynebacterium glutamicum*, a polypeptide encoded by the polynucleotide, a recombinant vector comprising the polynucleotide, a transformant capable of producing L-arginine in a high yield, which is prepared by introducing the recombinant vector into an L-arginine producing host microorganism to overexpress the argD2 gene, and a method for producing L-arginine by culturing the transformant. The transformant of the present invention overexpresses the argD2 gene to produce L-arginine in a high yield, thereby being used in medicinal and pharmaceutical industries.

4 Claims, 1 Drawing Sheet

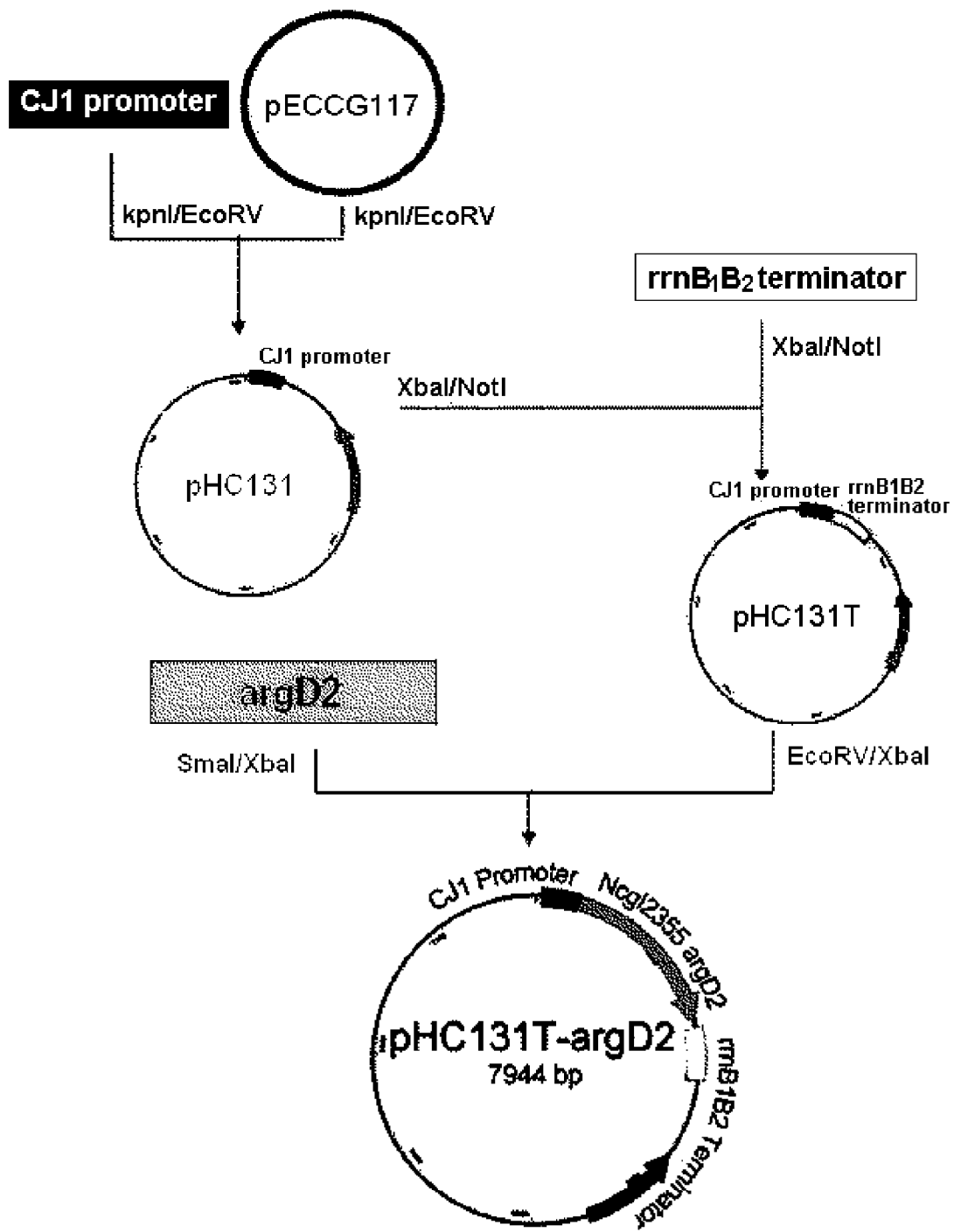
[Fig. 1]

US 8,048,648 B2

CORYNEBACTERIUM GLUTAMICUM VARIETY PRODUCING L-ARGININE AND METHOD FOR FABRICATING THE SAME

This application claims priority to PCT Application Serial No. PCT/KR2008/000204 filed Jan. 11, 2008 published in English on Jul. 24, 2008 as PCT WO 2008/088148 and also to Korean Application No. 10-2007-0005831 filed Jan. 18, 2007, the entire contents of each are incorporated herein by reference.

TECHNICAL FIELD

The present invention relates to an L-arginine producing mutant strain, which produces L-arginine in a high yield to be used in medicinal and pharmaceutical industries, and a method for fabricating the same. In particular, the present invention relates to a polynucleotide comprising an argD2 gene (Ncgl2355) which is a putative gene of acetylornithine aminotransferase involved in arginine biosynthesis of *Corynebacterium glutamicum*, a polypeptide encoded by the polynucleotide, a recombinant vector comprising the polynucleotide, a transformant capable of producing L-arginine in a high yield, which is prepared by introducing the recombinant vector into an L-arginine producing host microorganism to overexpress the argD2 gene, and a method for producing L-arginine by culturing the transformant.

BACKGROUND ART

L-arginine is a free-form amino acid found in plant seeds or garlic. L-arginine has been widely used as an efficient additive in medicaments, food, or the like. L-arginine is useful as a drug for improving the hepatic function and brain function, and treating male sterility, and as an ingredient of multiple amino acid supplements. Also, L-arginine has been used as a food additive in fish cakes and health beverages, and has recently gained interest as a salt substitute for hypertension patients.

Conventional methods for L-arginine production by biological fermentation are based on the production of L-arginine directly from carbon and nitrogen sources. For example, L-arginine can be produced using a mutant strain derived from a glutamic acid-producing microorganism belonging to the genus *Brevibacterium* or *Corynebacterium* (Japanese Unexamined Patent Publication Nos. Sho57-163487, Sho60-83593 and Sho62-265988), or using an amino acid-producing microorganism, of which growth properties are improved through cell fusion (Japanese Unexamined Patent Publication No. Sho59-158185). Recently, it has been reported that L-arginine can be produced using a recombinant strain, of which an argR gene that participates in regulation of arginine biosynthesis is inactivated (US Patent Application No. 2002/0045223A1) and using a method for over-expressing an argF gene of arginine operon (Korean Patent Application No. 10-2004-107215).

In microorganisms, biosynthesis of L-arginine proceeds in eight enzymatic steps starting from the precursor L-glutamate and follows two different pathways, the linear pathway or the cyclic pathway.

In microorganisms belonging to the genus *Corynebacterium*, L-arginine is synthesized through the cyclic pathway from L-glutamate via N-acetylglutamate, N-acetylglutamyl phosphate, N-acetylglutamate semialdehyde, N-acetylornithine, ornithine, citrulline and argininosuccinate. These intermediates are synthesized through consecutive reactions catalyzed by enzymes such as glutamate N-acetyltransferase, N-acetylglutamate kinase, acetylglutamate semialdehyde dehydrogenase, acetylornithine aminotransferase, ornithine cabomoyltransferase, arginosuccinate synthase, and arginosuccinate lyase. These enzymes are encoded by argJ, argB, argC, argD, argF, argG and argH genes, respectively.

In order to produce L-arginine in a high yield, the present inventors have conducted studies on the enzymes involved in L-arginine biosynthesis for a long period time. They found that in the intermediate step of arginine biosynthesis, the enzymatic reaction involved in the conversion of N-acetylglutamate semialdehyde to N-acetylornithine is amplified to increase L-arginine flux, thereby improving the productivity of L-arginine.

A variety of aminotransferases are present in cells, and divided into four subgroups on the basis of their mutual structural relatedness. Subgroup I comprises aspartylornithine, alanine, tyrosine, histidiolphosphate, and phenylalanine aminotransferases, subgroup II comprises acetylornithine, ornithine, ω-amino acid, aminobutyrate, and phenylalanine aminotransferases, subgroup III comprises D-alanine and branched-chain amino acid aminotransferases, and subgroup IV comprises serine and phosphoserine aminotransferases (Perdeep K. MEHTA, et al, *Eur. J. Biochem.*, 214, 549-561, 1993).

It has been known that in *Corynebacterium glutamicum*, an argCJBDF gene involved in arginine biosynthesis exists as an operon, and is regulated by feedback-inhibition due to arginine (Vehary Sakanyan, et al, *Microbiology*, 142:9-108, 1996). Thus, there is a limit in producing L-arginine in a high yield.

DISCLOSURE OF INVENTION

Technical Problem

Accordingly, the present inventors have made an effort to develop strains capable of producing L-arginine in higher yield. They found that a microorganism transformed with an argD2 gene, which is a putative gene having the same function as an argD gene encodingacetylornithine aminotransferases, overexpresses the argD2 gene and produces L-arginine in higher yield than a parent strain, thereby completing the present invention.

Technical Solution

It is an object of the present invention to provide a polypeptide encoded by an argD2 gene(Ncgl2355) that is a putative gene of acetylornithine aminotransferase involved in arginine biosynthesis of *Corynebacterium glutamicum*.

It is another object of the present invention to provide a recombinant vector comprising a base sequence encoding the polypeptide.

It is still another object of the present invention to provide a transformant capable of producing L-arginine in a high yield, which is prepared by introducing the recombinant vector.

It is still another object of the present invention to provide a method for producing L-arginine by culturing the transformant.

BRIEF DESCRIPTION OF THE DRAWINGS

FIG. 1 illustrates the construction of a recombinant plasmid pHC131T-argD2, comprising an argD2 gene, CJ1 promoter and rrnB$_1$B$_2$ terminator.

BEST MODE FOR CARRYING OUT THE INVENTION

In one embodiment, the present invention provides a polypeptide encoded by an argD2 gene (Ncgl2355) which is a putative gene of acetylornithine aminotransferase involved in arginine biosynthesis of *Corynebacterium glutamicum*. Preferably, an amino acid sequence of the polypeptide may be represented by SEQ ID NO. 1.

The argD2 gene (Ncgl2355) which is a putative gene of acetylornithine amino-transferase involved in arginine biosynthesis of *Corynebacterium glutamicum* is an aminotransferase classified into subgroup II according to genome based analysis (Alice C. McHardy, et al, *J. Biotechnology*, 104, 229-240, 2003), however, function of the protein encoded by the argD2 has not been clearly identified. There is a little sequence homology between argD and argD2 genes, however, both genes have the same motif, aminotransferase subgroup II. Therefore, it is inferred that the protein encoded by the argD2 gene has similar function to acetylornithine aminotransferase that is encoded by the argD gene and required for arginine biosynthesis (www.genome.jp/kegg/).

In a specific embodiment of the present invention, it can be seen that the L-arginine producing strain transformed with a recombinant vector comprising the argD2 gene produces L-arginine in higher yield than a parent strain.

In another embodiment of the present invention, the present invention provides a polynucleotide encoding an amino acid sequence of SEQ ID NO. 1. Preferably, the base sequence of the polynucleotide may be represented by SEQ ID NO. 2. Further, the present invention provides a polynucleotide having 70% or more homology with the base sequence of SEQ ID NO. 2, preferably 90% or more homology with the base sequence of SEQ ID NO. 2.

In still another embodiment of the present invention, the present invention provides a recombinant vector comprising the polynucleotide. Preferably, the recombinant vector may comprise the polynucleotide represented by SEQ ID NO. 2, and may be a recombinant vector pHC131T-argD2 prepared according to a specific embodiment of the present invention.

The recombinant vector may be easily fabricated by those skilled in the art according to any known method using DNA recombination technique. For example, in an embodiment of the present invention, the genomic DNA is isolated from the L-arginine producing strain, and PCR is performed using the isolated genomic DNA as a template to amplify the ORF region of argD2 gene. To fabricate a recombinant vector for overexpression, CJ1 promoter (Korean Patent No. 10-0620092) and rrnB$_1$B$_2$ terminator regions are amplified using pECCG117-CJ1 and *E. coli* K-12 as a template, respectively. The CJ1 promoter that is known as the upstream region of *Corynebacterium ammoniagenes* Hsp60 and strongly expressed in *Corynebacterium glutamicum*, and commercially available rrnB1B2 terminator are used as a promoter and terminator, respectively. In this connection, the base sequence of argD2 gene is analyzed by a conventional sequencing method. The promoter region, terminator region and argD2 gene are cloned into a suitable plasmid or other cloning vectors, and transformed into suitable competent cells to fabricate a recombinant vector (FIG. 1).

In the fabrication of the recombinant vector, any vector expressed in prokaryotic or eukaryotic cells may be used as a cloning vector, and in a specific embodiment of the present invention, a plasmid pECCG117 (Han J. K., et al, *Biotechnology letters*, 13(10):721-726, 1991 or Korean Patent Publication No. 92-7401) is used. Further, the L-arginine producing strain encompasses all microorganisms capable of producing L-arginine, including prokaryotic or eukaryotic cells, preferably *Escherichia coli, coryneform bacteria*, and *Bacillus* species capable of producing L-arginine, and more preferably *Corynebacterium glutamicum* capable of producing L-arginine.

In still another embodiment, the present invention provides a transformant capable of producing L-arginine in a high yield, which is prepared by introducing the recombinant vector into an L-arginine producing host microorganism to overexpress the argD2 gene.

Specifically, the host microorganism has a high DNA introduction efficiency and expression efficiency, and may be any microorganism capable of producing L-arginine, including prokaryotic or eukaryotic cells. The preferred Examples thereof include any one selected from the group consisting of the species *Escherichia, Aerobacter, Schizosaccharomyces, Pichia, Kluyveromyces, Candida, Hansenula, Debaryomyces, Zygosaccharomyces, Mucor, Torulopsis, Methylobacter, Salmonella, Bacillus, Streptomyces, Pseudomonas, Brevibacterium, Magnetospirillum* and *Corynebacterium*, more preferably microorganisms belonging to the genus *Corynebactrium*, which have a resistance to L-arginine analogues and produce L-arginine, and most preferably *Corynebacterium glutamicum* ATCC21493 or ATCC21831. Examples of the L-arginine analogues include an alpha-amino acid canavanine found in *Canavalia ensiformis* and arginine hydroxamate.

In a specific embodiment of the present invention, the recombinant vector pHC131T-argD2 is introduced into *Corynebacterium glutamicum* ATCC21493 and *Corynebacterium glutamicum* ATCC21831, which have a resistance to L-arginine analogues and produce L-arginine, so as to prepare transformed microorganisms CA06-0012 and CA06-0013. The transformed microorganisms CA06-0012 and CA06-0013 were deposited at the Korean Culture Center of Microorganisms (hereinafter, abbreviated to "KCCM" on Dec. 13, 2006 under accession number KCMM10820P and KCCM10821P, respectively.

The transformed microorganisms can be easily prepared by those skilled in the art according to any known method. The term "transformation" as used herein means introducing DNA into a host cell so that DNA is replicable, either as an extra-chromosomal element or by chromosomal integration, that is, artificial genetic alteration by introducing a foreign DNA into a host cell. Examples thereof include a CaCl$_2$ precipitation, a Hanahan method that is an improved CaCl$_2$ method by using DMSO (dimethyl sulfoxide) as a reducing material, electroporation, calcium phosphate precipitation, protoplast fusion, agitation using silicone carbide fiber, *Agrobacterium*-mediated transformation, PEG-, dextran sulfate-, and lipofectamine-mediated transformation. In one embodiment of the present invention, the recombinant vector pHC131T-argD2 was introduced into host cells by electroporation to prepare transformants, and a strain harboring the recombinant vector was selected using its antibiotic resistance.

To increase the L-arginine productivity of the transformant prepared according to the present invention, the argD2 gene present in the chromosome of the transformant may be additionally subjected to expression or deletion by a conventional recombinant technique. It is known in the related art that its base sequence can be analyzed by a sequencing method using fluorescence.

In the biosynthetic pathway of L-arginine, ornithine is an intermediate of the metabolic pathway of arginine and is an important material in nitrogen metabolism along with the urea cycle. The CA06-0012 and CA06-0013 strains transformed by the method of the present invention are transformants overexpressing the argD2 gene, prepared by the following method. The argD2 gene encoding a putative protein having a function of acetylornithine aminotransferase, which is obtained by PCR from the chromosome of the L-arginine producing strain *Corynebacterium glutamicum* ATCC21831, is inserted into a vector, and introduced into the L-arginine producing strains, *Corynebacterium glutamicum* ATCC21493 and ATCC21831. It was found that the transformed CA06-0012 and CA06-0013 strains according to the present invention overexpress the argD2 gene to increase the synthesis of N-acetylornithine, thereby activating the arginine biosynthetic pathway to produce L-arginine in a high yield.

Accordingly, in another embodiment, the present invention provides a method for producing L-arginine, comprising the step of culturing the transformant, preferably transformant represented by accession number KCCM10820P or KCCM10821P.

In the production method of L-arginine according to the present invention, the cultivation of the transformed L-arginine overexpressing microorganisms may be conducted in suitable media and under culture conditions known in the art. The culturing procedures can be readily adjusted by those skilled in the art according to the selected strain. Examples of the culturing procedures include batch type, continuous type and fed-batch type manners, but are not limited thereto. Various culturing procedures are disclosed in literature, for example, "Biochemical Engineering" (James M. Lee, Prentice-Hall International Editions, pp 138-176, 1991).

During cultivation, ammonium hydroxide, potassium hydroxide, ammonia, phosphoric acid, and sulfuric acid may be properly added to adjust the pH of the cultures. Defoaming agents such as fatty acid polyglycol ester may be properly added to reduce the formation of foams in cultures. Further, to maintain the cultures in aerobic states, oxygen or oxygen-containing gas (e.g., air) may be injected into the cultures. The cultures are maintained at 20 to 45° C. and preferably at 25 to 40° C. The cultivation may be continued until a desired amount of L-arginine is obtained, and preferably for 10 to 160 hrs. The isolation of L-arginine from the culture broth may be performed by the conventional method known in the art. Examples thereof may include centrifugation, filtration, ion-exchange chromatography, and crystallization. For example, the cultures may be subjected to low-speed centrifugation to remove the biomass, and the supernatant may be separated by ion-exchange chromatography.

MODE FOR THE INVENTION

Hereinafter, the present invention will be described in more detail with reference to Examples. However, these Examples are for the illustrative purpose only, and the invention is not intended to be limited by these Examples.

Example 1

Preparation of argD2 Gene, CJ1 Promoter and rrnB$_1$B$_2$ Terminator

To construct a recombinant vector pHC131T comprising an argD2 gene that is a putative gene of acetylornithine aminotransferase involved in arginine biosynthesis of *Corynebacterium glutamicum*, CJ1 promoter that is strongly expressed in *Corynebacterium glutamicum*, and rrnB$_1$B$_2$ terminator, a DNA fragment (1.371 Kb) including Open Reading Frame (hereinafter, abbreviated to "ORF") of argD2 gene was obtained from the genomic DNA (gDNA) of L-arginine producing strain ATCC21831, and PCR was performed using pECCG117-CJ1 (Korean Patent Application No. 10-2004-107215) and the genome of *E. coli* K-12 W3110 as a template to obtain the CJ1 promoter (0.3 Kb) and the rrnB$_1$B$_2$ terminator (0.4 Kb), respectively.

Example 1-1

Amplification of DNA Fragment Including ORF of argD2 Gene

The genomic DNA (gDNA) was extracted from L-arginine producing strain ATCC21831 using a Genomic-tip system (QIAGEN, hereinafter the same). In order to amplify the DNA fragment (1.371 Kb) including ORF of argD2 gene, polymerase chain reaction (hereinafter, abbreviated to "PCR") was performed using the gDNA as a template and a PTC-200 Peltier Thermal Cycler (MJ Research, USA, hereinafter the same). At this time, primers used in the amplification of the ORF region of argD2 gene were as follows: SEQ ID NO. 7; 5'-tccccccggggattggcatgaagggttac-3' and SEQ ID NO. 8; 5'-gctctagagcttagaacaacgccccagc-3'. PCR conditions included 25 cycles of denaturation at 94° C. for 30 sec, annealing at 55° C. for 30 sec and extension at 72° C. for 1 min. The PCR product was subjected to electrophoresis on a 1.0% agarose gel, and then a band of 1.3 kb was eluted from the gel.

Example 1-2

Amplification of CJ1 Promoter

To amplify the CJ1 promoter, PCR was performed using pECCG117-CJ1 (Korean Patent Application No. 10-2004-107215) as a template and a PTC-200 Peltier Thermal Cycler. At this time, primers used in the amplification of CJ1 promoter were as follows: SEQ ID NO. 3; 5'-cgggtaccac-cgcgggcttattccattacat-3' and SEQ ID NO. 4; 5'-acgcgatatct-taatctcctagattgggtttc-3'. PCR conditions included 25 cycles of denaturation at 94° C. for 30 sec, annealing at 55° C. for 30 sec and extension at 68° C. for 30 sec. The PCR product was subjected to electrophoresis on a 1.0% agarose gel, and then a band of 0.3 kb was eluted from the gel.

Example 1-3

Amplification of rrnB$_1$B$_2$ Terminator

The genomic DNA (gDNA) was extracted from *E. coli* K-12 W3110 using a Genomic-tip system. To amplify the rrnB$_1$B$_2$ terminator, PCR was performed using the gDNA as a template and a PTC-200 Peltier Thermal Cycler. At this time, primers used in the amplification of rrnB$_1$B$_2$ terminator were as follows: SEQ ID NO. 5; 5'-gctctagagctgttttggcggat-gaga-3' and SEQ ID NO. 6; 5'-ataagaatgcggccgccgcaaaaag-gccatccgtcag-3'. PCR conditions are the same as in the amplification of CJ1 promoter. The PCR product was subjected to electrophoresis on a 1.0% agarose gel, and then a band of 411 bp was eluted from the gel.

Example 2

Construction of Recombinant Plasmid

Example 2-1

Construction of Recombinant Plasmid pHC131T

A plasmid pECCG-117 (Han J. K., et al, *Biotechnology letters*, 13(10):721-726, 1991 or Korean Patent Publication No. 92-7401), which is an *E. coli/C. glutamicum* shuttle vector, was treated with restriction enzymes, EcoRV and KpnI, and then subjected to electrophoresis on a 0.8% agarose gel to elute a band of about 5.9 Kb. Further, the CJ1 promoter prepared in Example 1-2 was treated with restriction enzymes, KpnI and EcoRV, and then isolated using a Quiaquick PCR purification kit (Qiagen, hereinafter the same).

Two DNA fragments were ligated using a Quick ligation kit (NEB, hereinafter the same) to prepare a recombinant plasmid pECCG117-CJ1. The recombinant plasmid pECCG117-CJ1 was treated with restriction enzymes, XbaI and Not1, and then subjected to electrophoresis on a 0.8% agarose gel to elute a band of about 6.2 Kb. The prepared pECCG117-CJ1 and the rrnB$_1$B$_2$ terminator prepared in Example 1-3 were ligated using a Quick ligation kit to obtain a recombinant plasmid pECCG117-CJ1-rrnB$_1$B$_2$ (about 6.6 Kb), which was designated as "pHC131T" in the present invention.

The prepared pHC131T plasmid was treated with EcoRV and XbaI, and then subjected to electrophoresis on a 1% agarose gel to elute a band of about 6.6 Kb from the gel.

Example 2-2

Construction of Plasmid pHC131T-argD2

The PCR product of argD2 gene prepared in Example 1-1 was treated with restriction enzymes, smaI and XbaI, and then subjected to electrophoresis on a 0.8% agarose gel to elute a band of about 1.3 Kb from the gel. The resultant was ligated with pHC131T prepared in Example 2-1 using a Quick ligation kit, so as to construct a recombinant plasmid of about 7.4 Kb (FIG. 1), which was designated as "pHC131T-argD2" in the present invention.

Example 3

Sequencing Analysis of argD2 Gene

To analyze the base sequence of pHC131T-argD2 prepared in Example 2-2, PCR was performed using 0.1 ug DNA of pHC131T-argD2 as a template with 2 mM of a pair of primers of SEQ ID NOs. 3 and 6 and 1□ of a BigDye™ Terminator Cycle Sequencing v2.0 Ready Reaction (PE Biosystems). PCR conditions included 25 cycles of denaturation at 95° C. for 30 sec, annealing at 55° C. for 30 sec and extension at 72° C. for 2 min, followed by quenching at 4° C. to terminate the reaction. The PCR product was subjected to electrophoresis on a 0.8% agarose gel, and then a DNA fragment of 2 kb was eluted from the gel.

This DNA fragment was subjected to sequencing analysis using the primer of SEQ ID NO. 3 on an ABI PRISM 3100 Genetic Analyzer™ (Applied Biosystems). An amino acid sequence encoded by the argD2 gene of the present invention and a base sequence thereof are shown in SEQ ID NOs. 1 and 2, respectively.

Example 4

Preparation of Transformant

The recombinant plasmid pHC131T-argD2 prepared in Example 2-2 was introduced into L-arginine producing strains, ATCC 21493 and ATCC 21831 by electroporation to prepare transformants overexpressing the argD2 gene, which were designated as CA06-0012 and CA06-0013, respectively. The transformed microorganisms CA06-0012 and CA06-0013 were deposited at the Korean Culture Center of Microorganisms (hereinafter, abbreviated to "KCCM") on Dec. 13, 2006 under accession number KCMM10820P and KCMM10821P, respectively.

The strains and transformants were smeared on solid media containing 25 mg/L of Kanamycin (composition: 3.0 g/L of Beef extract, 5.0 g/L of peptone, hereinafter the same), and cultured at 30° C. for 16 hrs. The selected colonies were subjected to a flask titer test as the following Example 5. As a result, it was found that the argD2—overexpressing transformant according to the present invention produced L-arginine in a high yield.

Example 5

Comparison of Arginine Production Titer in Erlenmeyer Flask

Transformants prepared in Example 4 and parent strains, ATCC21831 and ATCC21493 were smeared on solid media containing 25 mg/L of Kanamycin, and cultured at 30° C. for 16 hrs to select 10 single colonies from each strain. The selected colonies were cultured in L-arginine seed media given in Table 1, and then evaluated for L-arginine productivity in an Erlenmeyer flask using titer media given in Table 1. The mean values of the L-arginine productivity were calculated and compared.

TABLE 1

| Ingredients | L-arginineseed media | L-argininetiter media |
| --- | --- | --- |
| Glucose | 5% | 4% |
| Bactopeptone | 1% | — |
| Sodium chloride (NaCl) | 0.25% | — |
| Yeast extract | 1% | — |
| Biotin | 3 ⎕/L | 200 ⎕/L |
| Urea | 0.4% | 0.3% |
| pH | 7.0 | 7.2 |
| Ammonium sulfate ((NH$_4$)$_2$SO$_4$) | — | 3% |
| Potassium Dihydrogen Phosphate (KH$_2$PO$_4$) | — | 0.1% |
| Potassium Monohydrogen Phosphate (K$_2$HPO$_4$) | — | 0.1% |
| Magnesium sulfate heptahydrate (MgSO$_4$7H$_2$O) | — | 0.025% |
| CSL (corn steep liquor) | — | 2.0% |

The selected colonies were inoculated in the seed media and cultured in an incubator at 30° C. for 16 hrs. 1 ml of the seed culture was inoculated in 24 ml of the titer media, and culturing was carried out at 30° C. and 220 rpm for 72 hrs. The results of L-arginine production titer test for ATCC21831, ATCC21493 and transformants are given in Table 2.

As shown in Table 2, the arginine producing strains *Corynebacterium glutamicum* ATCC 21493 and ATCC 21831 exhibited L-arginine productivity of 0.9 g/L and 4.4 g/L, respectively. Meanwhile, the argD2-overexpressing recombinant strains CA06-0012 and CA06-0013 of the present invention exhibited L-arginine productivity of 1.1 g/L and 4.9 g/L, respectively. It can be seen that the productivity of the recombinant strains CA06-0012 and CA06-0013 was increased by 0.2 g/L (22.2%) and 0.5 g/L (11.4%), as compared to each parent strain.

TABLE 2

| Productivity | Strain | | | |
|---|---|---|---|---|
| | Parent strain (ATCC21493) | Transformant (CA06-0012) | Parent strain (ATCC21831) | Transformant (CA06-0013) |
| L-arginine (g/L) | 0.9 | 1.1 | 4.4 | 4.9 |

It will be apparent to those skilled in the art that various modifications and changes may be made without departing from the scope and spirit of the invention. Therefore, it should be understood that the above Examples and Experimental Examples are not limitative, but illustrative in all aspects. The scope of the invention is defined by the appended claims rather than by the description preceding them, and therefore all changes and modifications that fall within meets and bounds of the claims, or equivalents of such meets and bounds are therefore intended to be embraced by the claims.

INDUSTRIAL APPLICABILITY

The present invention provides a polynucleotide comprising an argD2 gene (Ncgl2355) that is a putative gene of acetylornithine aminotransferase involved in arginine biosynthesis of *Corynebacterium glutamicum*, a polypeptide encoded by the polynucleotide, a recombinant vector comprising the polynucleotide, a transformant capable of producing L-arginine in a high yield, which is prepared by introducing the recombinant vector into an L-arginine producing host microorganism to overexpress the argD2 gene, and a method for producing L-arginine by culturing the transformant. The transformant of the present invention overexpresses the argD2 gene to produce L-arginine in a high yield, thereby being used in medicinal and pharmaceutical industries, and feed industry.

The invention claimed is:

1. A method for producing L-arginine, comprising the step of culturing a microorganism that is transformed with a recombinant vector comprising a polynucleotide encoding an argD2 polypeptide, wherein the argD2 polypeptide has an amino acid sequence consisting of SEQ ID NO. 1.

2. The method for producing L-arginine according to claim 1, wherein the polynucleotide has a nucleotide sequence consisting of SEQ ID NO. 2.

3. The method for producing L-arginine according to claim 1, wherein the microorganism belongs to the genus *Corynebacterium*.

4. The method for producing L-arginine according to claim 1, wherein the microorganism is identified by accession number KCCM10820P or KCCM10821P.

* * * * *

SEQUENCE LISTING

```
<160> NUMBER OF SEQ ID NOS: 8

<210> SEQ ID NO 1
<211> LENGTH: 456
<212> TYPE: PRT
<213> ORGANISM: Artificial Sequence
<220> FEATURE:
<223> OTHER INFORMATION: Amino acid sequence of synthetically produced
      ArgD2

<400> SEQUENCE: 1

Leu Thr Leu Lys Gly Tyr Thr Asn Phe Asp Gly Glu Phe Ile Glu Phe
1               5                   10                  15

Gly Ser Ala Gln Ala Lys Glu Glu Lys Arg Ala Phe Asp Asn Asp
            20                  25                  30

Arg Ala His Val Phe His Ser Trp Ser Ala Gln Asp Lys Ile Ser Pro
        35                  40                  45

Lys Val Trp Ala Ala Ala Glu Gly Ser Thr Leu Tyr Asp Phe Asp Gly
    50                  55                  60

Asn Ala Phe Ile Asp Met Gly Ser Gln Leu Val Ser Ala Asn Leu Gly
65                  70                  75                  80

His Asn Asn Pro Arg Leu Val Glu Ala Ile Gln Arg Gln Ala Ala Arg
                85                  90                  95

Leu Thr Asn Ile Asn Pro Ala Phe Gly Asn Asp Val Arg Ser Asp Val
            100                 105                 110

Ala Ala Lys Ile Val Ser Met Ala Arg Gly Glu Phe Ser His Val Phe
        115                 120                 125

Phe Thr Asn Gly Gly Ala Asp Ala Ile Glu His Ser Ile Arg Met Ala
    130                 135                 140

Arg Leu His Thr Gly Arg Asn Lys Ile Leu Ser Ala Tyr Arg Ser Tyr
145                 150                 155                 160

His Gly Ala Thr Gly Ser Ala Met Met Leu Thr Gly Glu His Arg Arg
                165                 170                 175

Leu Gly Asn Pro Thr Thr Asp Pro Asp Ile Tyr His Phe Trp Ala Pro
            180                 185                 190

Phe Leu His His Ser Ser Phe Phe Ala Thr Thr Gln Glu Glu Glu Cys
        195                 200                 205

Glu Arg Ala Leu Lys His Leu Glu Asp Val Ile Ala Phe Glu Gly Ala
```

```
            210                 215                 220
Gly Met Ile Ala Ala Ile Val Leu Glu Pro Val Gly Ser Ser Gly
225                 230                 235                 240

Ile Ile Leu Pro Pro Ala Gly Tyr Leu Asn Gly Val Arg Glu Leu Cys
            245                 250                 255

Asn Lys His Gly Ile Leu Phe Ile Ala Asp Glu Val Met Val Gly Phe
            260                 265                 270

Gly Arg Thr Gly Lys Leu Phe Ala Tyr Glu His Ala Gly Asp Asp Phe
            275                 280                 285

Gln Pro Asp Met Ile Thr Phe Ala Lys Gly Val Asn Ala Gly Tyr Ala
            290                 295                 300

Pro Leu Gly Gly Ile Val Met Thr Gln Ser Ile Arg Asp Thr Phe Gly
305                 310                 315                 320

Ser Glu Ala Tyr Ser Gly Gly Leu Thr Tyr Ser Gly His Pro Leu Ala
                325                 330                 335

Val Ala Pro Ala Lys Ala Ala Leu Glu Ile Tyr Ala Glu Gly Glu Ile
            340                 345                 350

Ile Pro Arg Val Ala Arg Leu Gly Ala Glu Leu Ile Glu Pro Arg Leu
            355                 360                 365

Arg Glu Leu Ala Glu Glu Asn Val Ala Ile Ala Asp Val Arg Gly Ile
370                 375                 380

Gly Phe Phe Trp Ala Val Glu Phe Asn Ala Asp Ala Thr Ala Met Ala
385                 390                 395                 400

Ala Gly Ala Ala Glu Phe Lys Glu Arg Gly Val Trp Pro Met Ile Ser
            405                 410                 415

Gly Asn Arg Phe His Ile Ala Pro Pro Leu Thr Thr Thr Asp Asp Glu
            420                 425                 430

Leu Val Ala Leu Leu Asp Ala Val Glu Ala Ala Gln Ala Val Glu
            435                 440                 445

Leu Thr Phe Ala Gly Ala Leu Phe
            450                 455

<210> SEQ ID NO 2
<211> LENGTH: 1371
<212> TYPE: DNA
<213> ORGANISM: Artificial Sequence
<220> FEATURE:
<223> OTHER INFORMATION: Nucleic acid sequence of synthetically produced
      ArgD2

<400> SEQUENCE: 2
ttgacactga agggttacac caactttgac ggtgaattca tcgaattcgg atctgcgcaa      60 gcaaagaag aggaaaaacg ggcattcgac aacgatcgcg cgcacgttt ccactcctgg      120 tccgcgcagg acaaaatcag ccccaaagta tgggcagctg ccgaaggttc cacgctgtac      180
gacttcgacg gcaacgcctt catcgacatg ggttcccaac ttgtctcggc aaacttaggc      240
cacaacaacc ctcgattagt tgaggcgatc cagcgccaag cagcccggtt gaccaacatc      300
aacccggctt tcggcaatga tgtgcgctct gatgttgctg caaagatcgt gtcgatggcc      360
cgtggcgaat tctcccacgt gttttttcacc aacggcggcg ccgacgccat cgaacactcc      420
atccgcatgg ctcgcctgca caccggacgc aacaaaattc tgtccgcata ccgcagctac      480
cacggcgcaa ccggatccgc gatgatgctc accggcgaac accgccgcct gggcaacccc      540
accaccgacc cagatatcta ccacttctgg gcaccattcc tgcaccactc ctcattcttt      600
gccaccaccc aagaagaaga atgcgaacgc gcactcaagc acttggaaga tgtcatcgcg      660
```

```
tttgaaggtg ctggcatgat cgcagcgatc gtcctggagc cagtggtggg atcatcagga    720
atcatcctgc caccagcagg ttacttaaat ggcgtgcgcg aactttgcaa caagcacggc    780
atcctcttca tcgccgacga agtcatggtc ggattcggac gcaccggaaa actgtttgct    840
tacgagcatg ctggcgacga tttccagcca gacatgatca ccttcgccaa gggtgttaac    900
gcaggttacg ccccactcgg tggcatcgtg atgacccaat caatccgcga taccttcgga    960
tcagaggcat actccggcgg actcacctac tccggacacc cacttgcagt agcacccgcc   1020
aaggcagcgc tggagattta cgcggaagga gagatcattc cacgcgtagc tcgacttggc   1080
gctgaactga tcgaacctcg ccttcgtgaa ctagcggaag aaaacgtagc gatcgctgac   1140
gtgcggggca tcggattctt ctgggcagtg gagttcaatg cagacgccac tgccatggct   1200
gccggtgctg cagaattcaa ggaacgcggc gtgtggccga tgatctccgg caaccgattc   1260
cacatcgcgc cgccgctgac caccactgat gacgaattgg tagcactgct ggacgcggtg   1320
gaagctgcag cccaagctgt cgagctgacc ttcgctgggg cgttgttcta a            1371
```

```
<210> SEQ ID NO 3
<211> LENGTH: 31
<212> TYPE: DNA
<213> ORGANISM: Artificial Sequence
<220> FEATURE:
<223> OTHER INFORMATION: Forward primer for PCR of CJ1 promoter

<400> SEQUENCE: 3
cgggtaccac cgcgggctta ttccattaca t                                    31

<210> SEQ ID NO 4
<211> LENGTH: 32
<212> TYPE: DNA
<213> ORGANISM: Artificial Sequence
<220> FEATURE:
<223> OTHER INFORMATION: Reverse primer for PCR of CJ1 promoter

<400> SEQUENCE: 4
acgcgatatc ttaatctcct agattgggtt tc                                   32

<210> SEQ ID NO 5
<211> LENGTH: 27
<212> TYPE: DNA
<213> ORGANISM: Artificial Sequence
<220> FEATURE:
<223> OTHER INFORMATION: Forward primer for PCR of rrnB1B2 Terminator

<400> SEQUENCE: 5
gctctagagc tgttttggcg gatgaga                                         27

<210> SEQ ID NO 6
<211> LENGTH: 37
<212> TYPE: DNA
<213> ORGANISM: Artificial Sequence
<220> FEATURE:
<223> OTHER INFORMATION: Reverse primer for PCR of rrnB1B2 Terminator

<400> SEQUENCE: 6
ataagaatgc ggccgccgca aaaggccat ccgtcag                               37

<210> SEQ ID NO 7
<211> LENGTH: 29
<212> TYPE: DNA
<213> ORGANISM: Artificial Sequence
<220> FEATURE:
<223> OTHER INFORMATION: Forward primer for PCR of argD2 gene's ORF
```

-continued

```
<400> SEQUENCE: 7 tccccgggg gattggcatg aagggttac                                      29

<210> SEQ ID NO 8
<211> LENGTH: 28
<212> TYPE: DNA
<213> ORGANISM: Artificial Sequence
<220> FEATURE:
<223> OTHER INFORMATION: Reverse primer for PCR of argD2 gene's ORF

<400> SEQUENCE: 8
gctctagagc ttagaacaac gccccagc                                      28
```